United States Patent
Roggiero et al.

[11] Patent Number: 5,939,092
[45] Date of Patent: Aug. 17, 1999

[54] COMPOSITION AND METHOD OF TREATMENT OF ANHIDROSIS IN HORSES

[76] Inventors: Pablo Roggiero, Santiago #322 y Manuel Larrea, Quito, Ecuador; Santiag Borja Cevallos, 540 Brickell Key Drive, Brickell Tower, Apt. 1107, Miami, Fla. 33131

[21] Appl. No.: 08/946,179

[22] Filed: Oct. 7, 1997

[51] Int. Cl.⁶ .............................. A23K 1/00; A61D 7/00
[52] U.S. Cl. .......................... 424/442; 424/637; 426/53; 426/54
[58] Field of Search .................................. 424/442, 637; 426/53, 54

[56] References Cited

U.S. PATENT DOCUMENTS

| | | |
|---|---|---|
| 4,072,742 | 2/1978 | Bouillon et al. . |
| 4,235,873 | 11/1980 | Packman . |
| 4,263,274 | 4/1981 | Kulkarni et al. . |
| 4,301,794 | 11/1981 | Tapper . |
| 4,325,367 | 4/1982 | Tapper . |
| 4,340,047 | 7/1982 | Tapper et al. . |
| 4,386,062 | 5/1983 | Beadle . |
| 4,764,532 | 8/1988 | Corman et al. . |
| 4,777,089 | 10/1988 | Takizawa et al. . |
| 4,889,711 | 12/1989 | Kai et al. . |
| 5,011,846 | 4/1991 | Gittos et al. . |
| 5,053,222 | 10/1991 | Takasu . |
| 5,200,315 | 4/1993 | Sutton et al. . |
| 5,276,056 | 1/1994 | LeRoy . |
| 5,330,891 | 7/1994 | Sutton et al. . |
| 5,461,142 | 10/1995 | Forssmann et al. . |
| 5,556,786 | 9/1996 | Kere et al. . |
| 5,604,205 | 2/1997 | Makarov et al. . |

*Primary Examiner*—Thurman K. Page
*Assistant Examiner*—Brian K. Seidleck
*Attorney, Agent, or Firm*—Lott & Friedland, P.A.

[57] ABSTRACT

A composition and method of treatment of anhidrosis in horses and other animals wherein the horses or other animals are given three dosages of sublimed sulfur and powdered milk sugar daily.

2 Claims, No Drawings

COMPOSITION AND METHOD OF TREATMENT OF ANHIDROSIS IN HORSES

TECHNICAL FIELD

The present invention relates generally to a composition and method for treating animal anhidrosis, and this invention specifically relates to a method of administering a substance composed of sublimed sulfur and powdered milk sugar to horses to alleviate the symptoms of anhidrosis in horses.

BACKGROUND OF THE INVENTION

In many tropical and semi-tropical regions, it is important to identify horses having inadequate thermal regulatory responses to hot, humid climates ("anhidrotic horses"). Anhidrosis is the incapacity of horses or other animals to perspire in response to adequate stimulation. It affects horses of any age, race or color. Though it has been reported that horses with rigorous training for racing, polo or jumping, or with highly concentrated diets, are more susceptible, recent studies show that mother mares and inactive horses get sick with the same frequency. Anhidrosis was first described by T. W. Wright and T. C. Tull in Vet. J. 81: 235–239 (1925), incorporated herein by reference. Such anhidrotic horses are not able to work or exercise strenuously because of their inability to adequately dissipate body heat in such climates, since sweating is the primary mechanism for heat dissipation in horses. This topic was discussed by Correa and Calderin in the Journal of the American Veterinary Medicine Association (J.A.V.M.A.), *Anhydrosis, Dry-Coat Sundrome in the Thoroughbred*, Vol. 149, December 1966, pp. 1556–1560, incorporated herein by reference. A number of possible causes of equine anhidrosis have been considered, but none have been established; therefore treatment has been empirical.

According to Arthur C. Guyton in *Textbook of Medical Physiology*, Chap. 73, (1992), when reference is made to different forms of heat loss, it involves irradiation, conduction and evaporation, it being indicated that 22% of heat is lost through evaporation, and that if adequate evaporation is prevented for any reason when the ambient temperature is greater than the body temperature, it will allow the body temperature to rise. There exists a temperature control system that utilizes three major mechanisms to reduce body heat when temperature increases excessively: (1) vasodilatation, (2) sweating, and (3) decreased heat production. When there is no sweating, there cannot be evaporation and such 22% heat loss would not exist. Hence, that heat would remain in the body.

Equine anhidrosis, first reported in British thoroughbreds taken to tropical colonies early in this century, is also known as "non-sweating", "dry-coat syndrome", "blowing" or "puff disease", and is manifested by ineffective sweating in response to appropriate stimuli. Sweat evaporation is the primary cooling mechanism for horses when the ambient temperature exceeds the body temperature. Anhidrotic horses have compromised thermoregulatory function and are in great danger of hyperthermia. Normal equine rectal temperature is about 99.5–101.5° F.; if asked to perform at extremely high ambient temperatures, anhidrotic horses have been known to achieve rectal temperatures of 108° F. and may collapse and die if raced. Providing shade or decreasing activity gives these horses only minimal relief.

Clinical features, pathogenesis and background of equine anhidrosis are described in U.S. Pat. No. 5,276,056 to LeRoy, incorporated herein by reference. The signs most commonly observed at the onset of anhidrosis are rapid breathing (tachypnea), the most common sign reported, fatigue, low tolerance to exercise and hair loss, especially in the face. Occasionally there is a slight loss of appetite, changes in water consumption and loss of general health. The commencement of the affliction usually starts during spring and summer, and can be abrupt or gradual. Many horses will maintain sweating under their manes and above their chests, with little or none produced in the rear. Partial anhidrosis can resolve itself in the winter, where apparently normal perspiration occurs.

Diagnosis of anhidrosis is based on small amounts of sweating produced during adequate stimulation. The affected horses heave, displaying rapid breathing during warm seasons. The rectal temperature could be highly elevated. In anhidrotic horses, there are not remarkable changes in the horse's hematology, electrolytes and enzymes, nor do skin biopsies allow for diagnosis. However, inadequate glandular response can be confirmed by administering intravenous epinephrine. See article by Warner, "*Anhidrosis*", *Current Therapy in Equine Medicine 2*, W. B. Saunders Company, 1987.

While the pathogenesis of anhidrosis is not known for certain, it has been suggested that its cause is a low regulation of the Beta-2 receptors of the sweat glands in response to abnormal concentration of highly circulating epinephrine, secondary to stress from heat. It is also possible that the process of secretion of the sweat glands will become fatigued after a prolonged demand. Certain characteristics of anhidrosis, such as dry skin, hair loss and decreased tolerance to exercise in heat, have led to the suggestion that hyperthyroidism is a contributing factor. However, there does not appear to be available evidence to confirm this suggestion.

Experiments in animals, whether large or small, have been conducted on a regular basis. In homeopathy, experiments can only be conducted in apparently healthy humans. In the book entitled *Pure Medical Matter*, Vol. 11, pp. 610–611, (reprint, 1980), Samuel Hahnemann describes anhidrosis-related experiments he conducted on humans. He conducted these experiments on humans because humans can better express the symptoms felt, and he carried them out on apparently healthy subjects. Being healthy, they showed no signs of any unbalance, that is, of any disease, and these subjects were capable of being objective and of describing the symptoms brought about by the experimental medication. The medication under study was administered to the subjects by giving repeated dosages three time daily. With the intake of repeated dosages of the medication, the bodies of the subjects had to produce an artificial disease caused by the experimental medication.

Symptoms related to skin, sweating and hair were among the many symptoms reported by the subjects. For example, the subjects reported falling out of the hair, especially on the head; complete anorexia; skin cracks here and there, especially in the open air; and scales and pruritus. More symptoms were also reported in *The Guiding Symptoms* of C. Hering, M.D., Vol. 10, pp. 96–193.

In this case, all of the experience gathered with humans was used to treat horses. Anhidrotic horses have been treated with various formulations with varying degrees of effectiveness. Various empirical treatments have been attempted to induce sweat in affected horses, with poor and varied results. These treatments include intravenous and oral administration of electrolytes and vitamin E. There have been efforts to provide horses with cold or at least cooler environments, by using fans or giving shade to the horse. Some have shaved the horses' bodies and moistened the bodies with water to provoke temperature loss through evaporation. Some exercise their horses during the cooler hours of the day.

One possible solution to this problem is to provide an oral composition to an anhidrotic horse which is effective in reducing the symptoms and illness associated with anhidrosis.

Another possible solution to this problem is to provide a treatment for anhidrosis which does not limit the climates or times of day when a horse can exercise and/or race.

Another possible solution to this problem is to provide a treatment for anhidrosis which does not require injections or shaving of a horse's body.

Thus, there has been a need in the art for an oral composition to an anhidrotic horse which is effective in reducing the symptoms and illness associated with anhidrosis.

There has been an additional need in the art for a treatment for anhidrosis which does not limit the climates or times of day when a horse can exercise and/or race.

There is yet another need in the art for a treatment for anhidrosis which does not require injections or shaving of a horse's body.

SUMMARY OF THE INVENTION

Generally described, the present invention solves significant problems in the art by providing a composition and method for the effective treatment of anhidrosis in horses and other animals without limiting the climate or time of day for exercising or racing and without need for injections or shaving the animal.

An object of the invention is to provide an oral composition to an anhidrotic horse which is effective in reducing the symptoms and illness associated with anhidrosis.

Another object of the invention is to provide a treatment for anhidrosis which does not limit the climates or times of day when a horse can exercise and/or race.

Another object of the invention is to provide a treatment for anhidrosis which does not require injections or shaving of a horse's body.

DETAILED DESCRIPTION OF THE PREFERRED EMBODIMENTS

The composition of the invention includes sulfur and milk sugar. Sulfur has the following properties: atomic weight, 32.97; atomic number, 16; density, 2.07 grams per cubic centimeter; boiling point, 444.6° C. Sulfur is a fine, yellow, somewhat greenish and gritty powder, having a slight odor and a faintly acid taste. It is insoluble in water and is slightly soluble in alcohol, varying depending upon the temperature and the physical form of the sulfur itself. Sulfur exists in three forms: crystalline, amorphous, and as a soft or oily substance. It is mostly abundantly obtained from native sulfur found in Italy and Sicily, but is widely distributed in nature in combination with many metals forming sulfides.

The composition of the invention is made according to methods used by homeopathic pharmacopoeia. The composition is prepared according to French pharmacopoeia, "the first liquid hahnemanian dilution (first LM or first 50,000) is obtained after the hahnemanian third centecimal". There are three types of scales in homeopathy whereby the medication is diluted or ground so that its concentration will be lowered: $1/10$ decimal scale; $1/100$ centesimal scale; $1/50,000$ fifty-thousandth scale or LM scale (in Roman numerals L=50 and M=1000, which means 50,000). In the decimal scale, 1 part of the medicinal substance is mixed with 9 parts alcohol or water to dilute, or milk sugar to grind, whereby a $1/10$ substance is obtained. The resulting product is called first decimal. In the centesimal scale, 1 part of the medicinal substance is mixed with 99 parts alcohol or water to dilute, or milk sugar to grind, whereby a $1/100$ substance is obtained. The resulting product is called first centesimal. If 1 part of the first centesimal is mixed with 99 parts alcohol or water to dilute, or milk sugar to grind, we will obtain a $1/10,000$ substance. This resulting product is called second centesimal. If 1 part of the second centesimal is mixed with 99 parts alcohol or water to dilute, or milk sugar to grind, we will obtain a $1/1,000,000$ substance. This resulting product is called third centesimal, and so on thereafter as far as this scale is concerned. In the fifty thousandth scale ($1/50,000$ or LM scale) in which the first 50,000 or first LM is prepared out of the third centesimal, the procedure is the following: We take 1 part of the $1/1,000,000$ concentration in the bottle containing the third centesimal and mix it with 500 parts of 90% alcohol. Then we take 1 part from this mixture and mix it with another 100 parts of alcohol, thereby obtaining a dilution 50,000 times lower than the former (third centesimal). This resulting product is stored in a bottle labeled as follows: 0/1, or First LM, or First fifty-thousandth. If we take 1 part from the bottle where the 0/1, of First LM, or First fifty thousandth is stored and mix it with 500 parts and then with 100 parts, we will again obtain a dilution 50,000 times lower than the previous one. This result should be labeled as follows: 0/2, or Second LM, or Second fifty-thousandth, and so on thereafter. See, e.g., *The Homeopathic Pharmacopoeia of the United States*, 8th Ed., Vol. I, 1979; *Farmacopeia Homeopatica Brasileira*, First Ed., 1976; *Pharmacotechnie et Monographies des Medicaments Courants*, Vol. II, 1979; *Farmacopea Homeopatica* of Dr. Wilmar Schwabe, Leipzig, 1929.

To be able to make the above-mentioned dilution, the sulfur must first be ground (see *Organon of Medicine* of Samuel Hahnemann, ¶270) until the one one-millionth attenuation (third centesimal grinding) is attained. Approximately five centigrams of sulfur is first ground according to the following grinding technique: a glazed porcelain mortar, the bottom of which has been turned dull with fine and moist sand, is used. After dividing five grams of milk sugar in three equal parts, to obtain approximately 1.67 grams per part, the first 1.67 grams is poured into the mortar. Approximately five centigrams of the sulfur substance, reduced to powder, is added to the top of this excipient to form a first mixture. The milk sugar used for dynamization should be of prime quality and perfectly pure. Dynamization is the dilution of medications followed by 100 blows over a thick book or object bound in leather. In a preferred embodiment one obtains milk sugar that is crystallized over yarn. The sulfur to be dynamized is mixed for a while with the milk sugar powder with a spatula, preferably made of porcelain. Then the first mixture is strongly ground for approximately six to seven minutes with a pounding mortar, also preferably porcelain, the bottom of which should also be dull. The first mixture from the bottom of the mortar, as well as the one adhering onto the pounding mortar, must be thoroughly scraped off and mixed using the spatula for three to four minutes to form a homogeneous mass. The mass is ground by exerting strong pressure for approximately six to seven minutes. Then the ground mass is again scraped off the bottom of the mortar and the pounding mortar and mixed for approximately three to four minutes.

The second 1.67 grams of the powdered milk sugar must then be added to the first mixture and mixed for a while with the spatula to form a second mixture. Once again the same force will be used to grind the second mixture for approximately six to seven minutes and once again all the second mixture adhered to the bottom of the mortar and the pounding mortar must be scraped off and mixed for approximately three to four minutes. The second mixture is then ground again for an additional approximately six to seven minutes, and then scraped off and mixed for another approximately three to four minutes.

The last 1.67 grams of the powdered milk sugar is then added to the second mixture and the material is mixed with the spatula, forming a third mixture. As in the previous steps, the third mixture is vigorously ground for approximately six to seven minutes, scraped off and mixed again for approximately three to four minutes, and finally ground for approximately six to seven minutes, followed by thoroughly scraping off all the mass to blend it carefully with the contents of the mortar.

The powder thus prepared must be kept away from the sunlight and daylight in a small, well-covered jar on which a label is pasted bearing the name of the substance, sulfur, and the number "100" (one one-hundredth attenuation) to indicate the first result.

To attain the one ten-thousandth attenuation, approximately five centigrams of the powder marked as "100" are poured into the mortar with approximately 1.67 grams of powdered milk sugar to form a "first 100th" mixture. This is mixed with the spatula and the above procedure is followed, carefully and vigorously grinding each one-third twice for approximately six to seven minutes, followed by scraping off and mixing for approximately three to four minutes before adding the second 1.67 grams of milk sugar to form a "second 100th" mixture and then the third 1.67 grams of milk sugar to form a "third 100th" mixture. Every time that another one-third of the powdered milk sugar is added, the operation must be repeated. Once the process is completed, the ground powder is put in a jar, carefully covered and labeled as "10,000".

Using the same procedure described above, approximately five centigrams of the one-ten thousandth preparation is mixed with approximately 1.67 grams of powdered milk sugar to form a "first 10,000th" mixture, a "second 10,000th" mixture, and a "third 10,000th" mixture, thereby lowering the concentration to the one-millionth attenuation, so that each five centigrams of the powder contains one one-millionth of the five centigrams of the initial substance.

In summary, each of the three preparations, to reach the third centesimal grinding, requires approximately six to seven minutes of grinding six times and approximately three to four minutes of scraping and mixing six times. Overall, approximately one hour of work is necessary per each degree of grinding. Following the first grinding that lasted one hour, in each five centigrams of powder, the preparation contains one one-hundredth ($\frac{1}{100}$) of the starting substance. Following the second operation, there will remain one ten thousandth ($\frac{1}{10,000}$) of the initial substance. Following the third and last operation, there will be one one-millionth ($\frac{1}{1,000,000}$) of the primitive substance.

The next step is to dissolve approximately five centigrams of the powder ground to the one one-millionth concentration (third centesimal grinding) in approximately five hundred drops of a solution prepared with one part 90% alcohol and four parts distilled water. Ethyl alcohol should be used. Then, one drop of this mother solution is added into a small jar containing one hundred drops of 95% alcohol. Once the small jar is carefully covered, it is hand-shaken vigorously one hundred times against a resilient and elastic object, for instance, a thick leather-bound book. This liquid constitutes the first degree of dynamization of the medicament.

This medicamentous dynamization in alcohol is placed in a small container, such as a cylindrical thimble-shaped container, made preferably of glass or porcelain, the bottom of which should be pierced with a small hole to saturate globules that are intended to be treated. The globules are small cane sugar bits of such a size that one hundred of them will not exceed five centigrams of weight. The dynamized medicament, as a 95% alcoholic solution, is poured over the globules to thoroughly soak them, and the liquid percolates through the pierced bottom of the container. The container is then turned over and shaken so that the globules fall over filter paper where they are spread out to quickly dry.

Once the globules are dry, they are placed in another jar that is immediately covered and labeled "I", for instance, to indicate the first degree of pharmaco-dynamic power. In order to obtain the next dynamization, a drop of water is put in another jar where only one of the small "I" globules is added to dissolve. After adding one hundred drops of 95% alcohol, it is dynamized by the same procedure described above, and strongly shaken one hundred times. This medicamentous dynamization in alcohol is used in the same manner to saturate five hundred new small granules that are also quickly spread over filter paper, dried and then kept in a clean and well-covered glass jar away from the heat and the daylight. This jar should be labeled "II", for instance, to indicate the second degree of power.

The same operation is repeated once more to obtain a dynamization in alcohol of one one-hundredth the concentration of the concentration achieved during the second dynamization set of steps. Globules from this step are then dissolved in one hundred drops of alcohol at 95% concentration and shaken one hundred times and then dried. These globules, when saturated prior to drying, represent the fourth degree of dynamization. The concentration of sublimate sulfur (washed) to 0/4, of fourth fifty thousandth, or 4 LM is $1.6 \times 10^{-25}$. The concentration of milk sugar (pure) and alcohol (90°) is irrelevant because these substances are used merely as a vehicle for the entire process.

The globules obtained from the fourth degree of dynamization have been administered to horses showing symptoms of anhidrosis, and the horses were cured of the disease. Horses have been treated with this medicamentous dosage in Miami, Fla. (eleven horses); Panama City, Panama (twenty-five horses); and Guayaquil, Ecuador (thirty-one horses). Almost all the horses treated were thoroughbred racehorses. Ninety-nine point three percent (99.3%) of the horses (sixty-seven horses) treated were cured. These dramatic cures, in most cases, have been evaluated and certified by veterinarians, trainers, and race course owners and managers. All of the horses treated and cured, except one removed for breeding, subsequently won several races.

The following are illustrative examples of the method of the invention:

Horse I

Horse I was a four-year old horse successfully performing as a racehorse until three years of age. At three years of age it began to have unsuccessful performances, developed agitated respiration even at rest, and ceased to sweat while racing, exercising or training. Its skin became dry and scaly, its coat dull, and its hair began to fall off its face. Treatment with sulfur 0/4 L.M. (four fifty-thousandths) was established.

Five milliliters of the medicament, 0/4 LM sulfur, were administered three times a day, half an hour from taking any other substance or feed, by suctioning the container ten times at each intake.

Thirty days later, the horse began to sweat after exercising and breathing improved. Thirty days later after the last administration of the medicament, the horse participated once again in a race and its performance was very good.

Horse II

Horse II was a seven-year old horse with excellent pedigree which for five years had participated in races with incredible success. It began to have breathing difficulties even at rest, stopped sweating, its skin became dry and brittle, and its coat became dull and brittle. After taking the medicament, 0/4 LM sulfur, for one month and in the same manner as administered to Horse I, Horse II began to sweat abundantly and in a foamy manner, and its breathing was no longer agitated. Horse II was again able to race. Although its performance on the race track was not the best for its age, being cured of anhydrosis, it was used as a breeder due to its pedigree.

Horse III

Horse III was a four year old horse used in racing, having performed excellently. It ceased racing for one year as it developed agitated respiration, even at rest, and did not sweat during training or exercising. Its skin was dry and brittle and its coat was dull and straw-like. After taking the medication for thirty days, 0/4 LM sulfur, the horse began to sweat profusely and the coat, skin and respiration improved. After thirty days from the last administration of the medicament, the horse returned to the race courses and won several races. Medication was administered as described above with respect to Horse I.

From the foregoing description those skilled in the art will appreciate that all of the objects of the present invention are realized. A composition and method of treating equine anhidrosis has been shown and described which alleviates the dangerous symptoms associated therewith and allows horses to successfully return to racing activities.

While specific embodiments have been shown and described, many variations are possible. This invention can be used on all living beings that are liable to suffer this disease. An example is dairy cattle because the disease can affect milk production. The same dosages and powers should be used for all treatments.

Having described the invention in detail, those skilled in the art will appreciate that modifications may be made of the invention without departing from its spirit. Therefore, it is not intended that the scope of the invention be limited to the specific embodiments illustrated and described. Rather, it is intended that the scope of the invention be determined by the appended claims and their equivalents.

What is claimed is:

1. A method of preparing a composition for treating anhidrosis, comprising the steps of:

mixing approximately 5 centigrams of sulfur and approximately 1.67 grams of milk sugar in a mortar to make a first mixture;

grinding said first mixture for approximately 6 to 7 minutes;

scraping said first mixture off the bottom of said mortar;

mixing said first mixture for approximately 3 to 4 minutes;

grinding said first mixture for an additional approximately 6 to 7 minutes;

mixing said first mixture for an additional approximately 3 to 4 minutes;

mixing said first mixture with approximately 1.67 grams of milk sugar to make a second mixture;

grinding said second mixture for approximately 6 to 7 minutes;

scraping said second mixture off the bottom of said mortar;

mixing said second mixture for approximately 3 to 4 minutes;

grinding said second mixture for an additional approximately 6 to 7 minutes;

mixing said second mixture for an additional approximately 3 to 4 minutes;

mixing said second mixture with approximately 1.67 grams of milk sugar to make a third mixture;

grinding said third mixture for approximately 6 to 7 minutes;

scraping said third mixture off the bottom of said mortar;

mixing said third mixture for approximately 3 to 4 minutes;

grinding said third mixture for an additional approximately 6 to 7 minutes;

mixing said third mixture for an additional approximately 3 to 4 minutes obtaining one-one hundreth ($1/100$) of the starting substance;

mixing approximately 5 centigrams of said one-one hundredth ($1/100$) sulfur and approximately 1.67 grams of milk sugar in a mortar to make a first 100th mixture;

grinding said first 100th mixture for approximately 6 to 7 minutes;

scraping said first 100th mixture off the bottom of said mortar;

mixing said first 100th mixture for approximately 3 to 4 minutes;

grinding said first 100th mixture for an additional approximately 6 to 7 minutes;

mixing said first 100th mixture for an additional approximately 3 to 4 minutes;

mixing said first 100th mixture with approximately 1.67 grams of milk sugar to make a second 100th mixture;

grinding said second 100th mixture for approximately 6 to 7 minutes;

scraping said second 100th mixture off the bottom of said mortar;

mixing said second 100th mixture for approximately 3 to 4 minutes;

grinding said second 100th mixture for an additional approximately 6 to 7 minutes;

mixing said second 100th mixture for an additional approximately 3 to 4 minutes;

mixing said second 100th mixture with approximately 1.67 grams of milk sugar to make a third 100th mixture;

grinding said third 100th mixture for approximately 6 to 7 minutes;

scraping said third 100th mixture off the bottom of said mortar;

mixing said third 100th mixture for approximately 3 to 4 minutes;

grinding said third 100th mixture for an additional approximately 6 to 7 minutes;

mixing said third 100th mixture for an additional approximately 3 to 4 minutes obtaining one ten thousandth ($1/10,000$) of the initial substance;

mixing approximately 5 centigrams of said one ten thousandth (1/10,000) sulfur and approximately 1.67 grams of milk sugar in a mortar to make a first 10,000th mixture;

grinding said first 10,000th mixture for approximately 6 to 7 minutes;

scraping said first 10,000th mixture off the bottom of said mortar;

mixing said first 10,000th mixture for approximately 3 to 4 minutes;

grinding said first 10,000th mixture for an additional approximately 6 to 7 minutes;

mixing said first 10,000th mixture for an additional approximately 3 to 4 minutes;

mixing said first 10,000th mixture with approximately 1.67 grams of milk sugar to make a second 10,000th mixture;

grinding said second 10,000th mixture for approximately 6 to 7 minutes;

scraping said second 10,000th mixture off the bottom of said mortar;

mixing said second 10,000th mixture for approximately 3 to 4 minutes;

grinding said second 10,000th mixture for an additional approximately 6 to 7 minutes;

mixing said second 10,000th mixture for an additional approximately 3 to 4 minutes;

mixing said second 10,000th mixture with approximately 1.67 grams of milk sugar to make a third 10,000th mixture;

grinding said third 10,000th mixture for approximately 6 to 7 minutes;

scraping said third 10,000th mixture off the bottom of said mortar;

mixing said third 10,000th mixture for approximately 3 to 4 minutes;

grinding said third 10,000 mixture for an additional approximately 6 to 7 minutes;

mixing said third 10,000th mixture for an additional approximately 3 to 4 minutes obtaining one one millionth (1/1,000,000) of the initial substance;

dissolving said one one millionth concentration (third centecimal grinding) mixture in a solution of 1 part 90% alcohol and 4 parts distilled water to create a mother solution;

mixing 1 drop of said mother solution with 100 drops of a 95% alcohol solution to create first dynamized solution;

shaking said first dynamized solution;

pouring said first dynamized solution over a first set of 500 sugar globules;

air-drying said first set of 500 sugar globules;

dissolving one globule of said first set of 500 sugar globules in 1 drop of water and 100 drops of a 95% alcohol solution to create a second dynamized solution;

shaking said second dynamized solution;

pouring said second dynamized solution over a second set of 500 sugar globules;

air-drying said second set of 500 sugar globules;

dissolving one globule of said second set of 500 sugar globules in 1 drop of water and 100 drops of a 95% alcohol solution to create a third dynamized solution;

shaking said third dynamized solution;

pouring said third dynamized solution over a third set of 500 sugar globules;

air-drying said third set of 500 sugar globules;

dissolving one globule of said third set of 500 sugar globules in 1 drop of water and 100 drops of a 95% alcohol solution to create a fourth dynamized solution;

shaking said fourth dynamized solution;

pouring said fourth dynamized solution over a fourth set of 500 sugar globules; and air-drying said fourth set of 500 sugar globules.

2. The method of claim 1 wherein said composition is used to treat animals suffering from anhidrosis by administering said fourth dynamized solution of said composition three times a day.

* * * * *